United States Patent
Giasson et al.

(10) Patent No.: US 8,949,730 B2
(45) Date of Patent: Feb. 3, 2015

(54) LIBRARY SELECTION IN DENTAL PROSTHESIS DESIGN

(75) Inventors: David Giasson, Québec (CA); Jean-Philippe Lajoie-Dorval, Québec (CA)

(73) Assignee: Biocad Medical, Inc., Nord Quebec (CA)

( * ) Notice: Subject to any disclaimer, the term of this patent is extended or adjusted under 35 U.S.C. 154(b) by 872 days.

(21) Appl. No.: 12/835,936

(22) Filed: Jul. 14, 2010

(65) Prior Publication Data

US 2012/0015328 A1 Jan. 19, 2012

(51) Int. Cl.
| | |
|---|---|
| G06F 3/048 | (2013.01) |
| A61C 11/00 | (2006.01) |
| A61C 5/10 | (2006.01) |
| A61C 13/00 | (2006.01) |
| A61C 7/00 | (2006.01) |

(52) U.S. Cl.
CPC ............ A61C 13/0004 (2013.01); A61C 7/002 (2013.01)
USPC ........... 715/771; 715/764; 433/213; 433/223; 433/196

(58) Field of Classification Search
CPC .......................... A61C 13/0004; A61C 7/002
USPC ................... 715/771, 764; 433/216, 223, 196
See application file for complete search history.

(56) References Cited

U.S. PATENT DOCUMENTS

| | | | |
|---|---|---|---|
| 5,273,429 A | 12/1993 | Nappi et al. | |
| 5,674,069 A | 10/1997 | Osorio | |
| 6,231,342 B1 | 5/2001 | Osorio et al. | |
| 6,328,567 B1 * | 12/2001 | Morris et al. | 433/215 |
| 7,134,874 B2 | 11/2006 | Chishti et al. | |
| 7,140,877 B2 | 11/2006 | Kaza | |
| 7,228,191 B2 | 6/2007 | Hofmeister et al. | |
| 2001/0021498 A1 | 9/2001 | Osorio et al. | |
| 2002/0028417 A1 * | 3/2002 | Chapoulaud et al. | 433/24 |
| 2002/0110786 A1 | 8/2002 | Dillier | |
| 2004/0185422 A1 | 9/2004 | Orth et al. | |
| 2004/0197727 A1 * | 10/2004 | Sachdeva et al. | 433/24 |
| 2004/0265770 A1 * | 12/2004 | Chapoulaud et al. | 433/24 |
| 2006/0008776 A1 | 1/2006 | Orth et al. | |
| 2006/0105294 A1 | 5/2006 | Burger et al. | |
| 2007/0207437 A1 * | 9/2007 | Sachdeva et al. | 433/24 |
| 2007/0292821 A1 * | 12/2007 | De Vreese | 433/195 |
| 2008/0015727 A1 | 1/2008 | Dunne et al. | |
| 2008/0096151 A1 * | 4/2008 | Cinader et al. | 433/24 |

(Continued)

OTHER PUBLICATIONS

Hans Geiselhoringer & Dr Stefan Hoist, Cusomized abutments for long-term aesthetics—software tools to meet clinical and laboratory requirements, 2009, Germany.*

(Continued)

*Primary Examiner* — Tadeese Hailu
(74) *Attorney, Agent, or Firm* — Knobbe Martens Olson & Bear, LLP

(57) ABSTRACT

Presented herein are techniques methods, systems, devices, and computer-readable storage media for library selection in dental prosthesis design. Embodiments include presenting two or more dental morphology libraries for use in a dental plan and receiving a selection of one or more tooth morphologies from one of the presented dental morphology libraries. The selected tooth morphologies can then be placed in the dental plan at particular tooth positions. An operator can also replace all tooth morphologies in a dental plan with those of a particular library or "mix and match" tooth morphologies from multiple libraries in a dental plan.

19 Claims, 9 Drawing Sheets

(56) References Cited

U.S. PATENT DOCUMENTS

| | | | |
|---|---|---|---|
| 2008/0261165 A1 | 10/2008 | Steingart et al. | |
| 2009/0133260 A1* | 5/2009 | Durbin et al. | 29/896.11 |
| 2009/0248184 A1* | 10/2009 | Steingart et al. | 700/98 |
| 2010/0151417 A1* | 6/2010 | Nilsson et al. | 433/167 |
| 2011/0196653 A1* | 8/2011 | Lajoie et al. | 703/1 |
| 2012/0015316 A1* | 1/2012 | Sachdeva et al. | 433/24 |
| 2012/0065985 A1* | 3/2012 | Royal et al. | 705/2 |

OTHER PUBLICATIONS

Hans Geiselhoringer & Dr Stefan Hoist, The new NobelProcera system for clinical success: The next level of CAD/CAM dentistry, Apr. 29, 2009, Germany.*

* cited by examiner

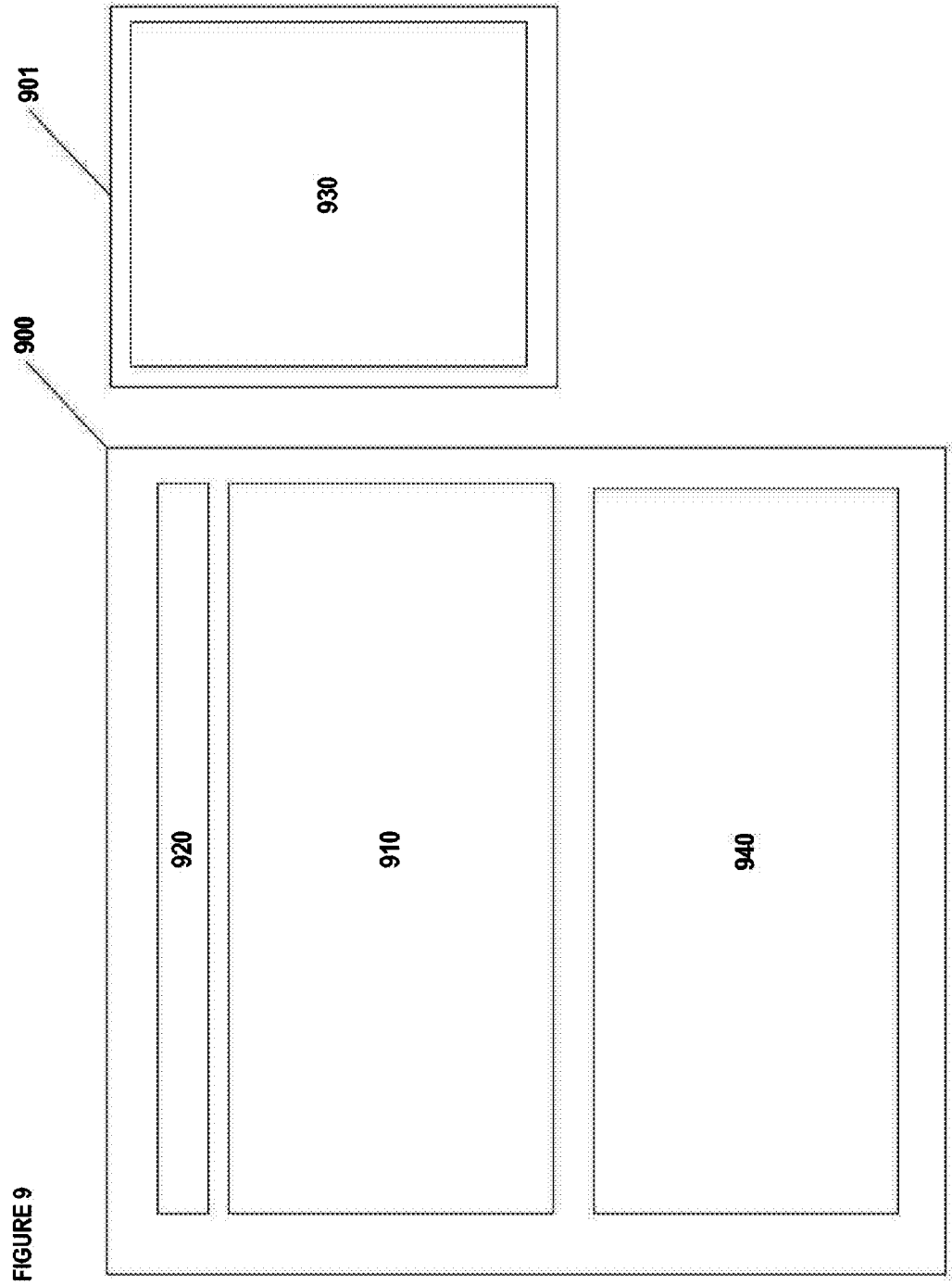

LIBRARY SELECTION IN DENTAL PROSTHESIS DESIGN

BACKGROUND

1. Field

The present application generally relates to dental planning, and more particularly to library selection in dental prosthesis design.

2. Description of related technology

The use of computer systems to design dental prostheses has increased in recent years. The computer systems allow a dentist, dental technician, or other operator to design dental prostheses for individual patients. These individual prosthesis designs are often called "situations," "dental plans," or "prosthetic plans." Operators, such as dentists, dental technicians, and others, using the computer systems can design plans based on a library of the teeth shapes and positions, patient data, and available equipment and hardware. For example, an operator may design a full-anatomic crown or bridge based on stored models of teeth. These stored models of teeth, together, may be called a library of teeth. A problem with current systems is that the models provided to the operator may not be appropriate for the dental prosthesis being designed. Another problem with current systems is that selecting the model(s) for use in the dental prosthesis design may be cumbersome.

These problems and others are addressed by the techniques, systems, methods, devices, and computer-readable storage media described herein.

SUMMARY

Presented herein are methods, systems, techniques, devices, and computer-readable storage media for library selection in dental prosthesis design. This summary in no way limits the invention herein, but instead is provided to summarize a few of the embodiments.

Embodiments herein include methods, systems, techniques, devices, and computer-readable storage media for library selection in dental prosthesis design, including, for example, presenting, via a computer-based interface running on one or more computer processors, two or more dental morphology libraries for use in a dental plan; receiving via the computer-based interface a selection of one or more tooth morphologies from among the tooth morphologies in a particular dental morphology library, said particular dental morphology library being selected from among the two or more dental morphology libraries; receiving via the computer-based interface placement information in the dental plan for the one or more tooth morphologies; and placing the one or more tooth morphologies in the dental plan. The methods, systems, techniques, devices, and computer-readable storage media may also include generating production data based on the placed one or more tooth morphologies.

Numerous other embodiments are described throughout herein.

For purposes of summarizing the invention and the advantages achieved over the prior art, certain objects and advantages of the invention are described herein. Of course, it is to be understood that not necessarily all such objects or advantages need to be achieved in accordance with any particular embodiment. Thus, for example, those skilled in the art will recognize that the invention may be embodied or carried out in a manner that achieves or optimizes one advantage or group of advantages as taught or suggested herein without necessarily achieving other objects or advantages as may be taught or suggested herein.

All of these embodiments are intended to be within the scope of the invention herein disclosed. These and other embodiments will become readily apparent to those skilled in the art from the following detailed description having reference to the attached figures, the invention not being limited to any particular disclosed embodiment(s).

BRIEF DESCRIPTION OF THE DRAWINGS

FIG. 9 illustrates a seventh interface for library selection in dental prosthesis design.

DETAILED DESCRIPTION OF SPECIFIC EMBODIMENTS

Overview

Figure 1:
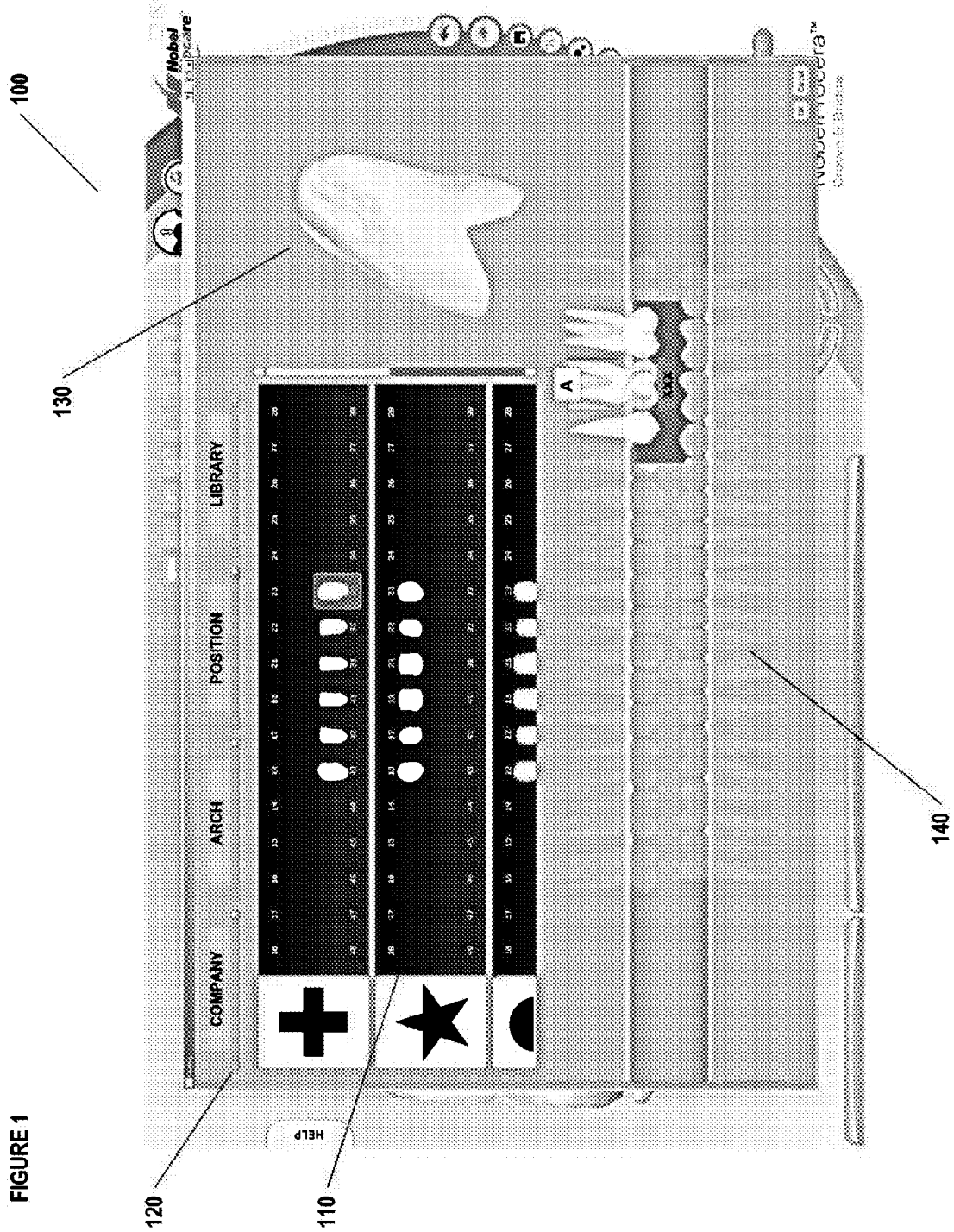
FIG. 1 illustrates a first interface for library selection in dental prosthesis design.

Current systems for designing dental prostheses use computers to enable dentists, dental practitioners and other operators to make and manipulate dental plans. The dental plans may include full anatomic restorations, sometimes known as full contour restorations, cut back restorations, or any other kind of restoration or dental prosthesis. The systems, methods, techniques, computer-readable storage media, and processes described herein allow the operator to select one or more morphologies for the dental plan with a simple and intuitive library interface. Groups of morphologies for teeth may, together, be an example of a "morphology library." For example, FIG. 1 illustrates a first interface for library selection in dental prosthesis design. An operator may design a dental plan in interface 100. While designing the dental plan, the operator may open up a window in interface 100 in order to select a morphology library to use in the dental plan—either for the whole dental plan or for one or more of the teeth in the dental plan. The interface 100 may include a library filter portion 120, a library selection portion 110, a tooth morphology preview portion 130, and/or a desired dental plan portion 140. These different portions may work in conjunction to provide the operator with the ability to select tooth morphologies to place in the dental plan.

In some embodiments, the operator may be able to filter the libraries shown in the library selection portion 110 by selecting filters in the library filter portion 120. Example filters include filtering by company(ies), by arch (e.g., mandibular or maxillary), by position (e.g., anterior or posterior), or by library or group of libraries. Once the libraries are filtered, they are displayed in the library selection portion 110. In FIG. 1 three libraries are depicted, one indicated with a plus symbol, another with a star symbol, and the top half of a third library is shown with a circle symbol. There may also be a scroll bar on the library selection portion to allow an operator to scroll up and down among the selectable libraries. The desired dental plan portion 140, in some embodiments, may illustrate 'active' and 'non-active' or 'inactive' tooth positions. The active tooth positions correspond to those that can be modified in the desired dental plan. The active tooth positions may be visually distinguishable by being more vividly shown, by using colors or shading, or via any appropriate technique. The non-active or inactive tooth positions may be those that are not modifiable in the desired dental plan. They may be shown without or with muted color, shading, etc.

In some embodiments, the operator can select one or more tooth morphologies using the mouse, keyboard, verbal cues, or any other method. In FIG. 1, the operator has selected a particular tooth morphology at tooth number "33" from the library represented by the plus symbol. That particular tooth morphology is shown in semi-realistic fashion in the preview portion 130. In some embodiments, the operator may drag the selected tooth down into the desired dental plan portion 140 in order to choose a morphology for a particular tooth. The operator may do this by clicking a mouse button on top of the tooth morphology in the library selection portion 110 and, while still holding the mouse button down, dragging that tooth morphology into the desired dental plan portion 140 over the desired tooth in the dental plan. The operator may choose which particular tooth to drop the tooth morphology in the desired dental plan portion 140 by releasing the mouse button when the dragged tooth morphology is over the desired tooth or unit position.

In various embodiments, an operator may select one or more tooth morphologies from a first library in the library selection portion 110 and place those in the desired dental plan portion 140 and select one or more tooth morphology from a different library in the library selection portion 110 and place those in other positions of the desired dental plan. For example, the operator may drag a tooth morphology from the "plus" library to, for example, tooth position 26 in the desired dental plan portion 140 to select that morphology for tooth position 26 and select a tooth morphology from the "star" library and drag it to tooth position 27 in the desired dental plan portion 140 to in order to select the "star" morphology for tooth position 27.

In some embodiments, the operator can drag an entire library into the desired dental plan portion 140 in order to select the morphologies in the library for use for all of the active positions in the desired dental plan. If there are already morphologies in use in the dental plan, dragging an entire library to the desired dental plan portion 140 may cause the selected library to replace the morphologies at all active tooth positions in the desired dental plan. More details and examples of these embodiments and other embodiments are discussed more throughout herein.

In various embodiments, after the operator has selected tooth morphologies for use in the desired dental plan, dental planning may continue. For example, the operator may modify the shape, position, or other characteristic of tooth morphologies in the desired dental plan. Examples of such additional planning are described in U.S. patent application Ser. No. 12/703,601, filed Feb. 10, 2010, entitled Dental Prosthetics Manipulation, Selection, and Planning, which is hereby incorporated by reference in its entirety for all purposes. Production data may then be generated based at least in part on the desired dental plan, including the selected tooth morphologies and the corresponding placements or other modifications made during subsequent dental planning. The production data may be used to manufacture, produce, or otherwise create dental prostheses.

Example System

Figure 2:
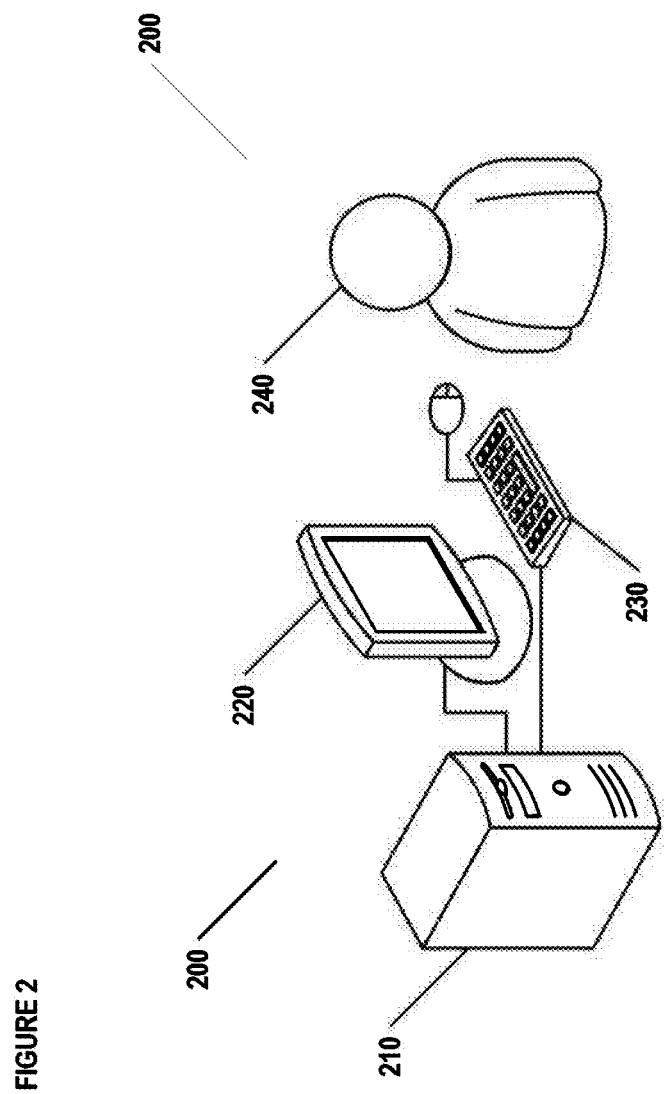
FIG. 2 illustrates an example system for library selection in dental prosthesis design.

FIG. 2 illustrates an example system 200 for library selection in dental prosthesis design. The system 200 may include one or more computers 210 coupled to one or more displays 220, and one or more input devices 230. An operator 240, who may be a dentist, dental technician, or other person, may plan dental prostheses using system 200 by manipulating the one or more input devices 230, such as a keyboard and/or a mouse. In some embodiments, while working on the dental plan, the operator 240 may view the dental plan and other related dental plan data on the display 220. The display 220 may include two or more display regions or portions, each of which displays a different view of the dental plan. For example, in some embodiments, the display 220 may show a semi-realistic 3D rendering of the dental plan, a localized abstraction of the dental plan, and/or a cross-sectional representation of the dental plan. Each of these displays or portions may be linked internally within a program and/or using data on computer 210. For example, a program running on a computer 210 may have a single internal representation of the dental plan in memory and the internal representation may be displayed in two or more abstract or semi-realistic manners on display 220. Modifying a desired dental plan may comprise modifying an underlying data model of the plan.

In some embodiments, the operator 240 may be able to perform a command, such as select, move, manipulate, or make transparent, opaque, or invisible, on a particular substructure in the dental plan. The operator 240 may be able to perform this command by manipulating the input device 230, such as clicking with a mouse on a particular region of one of the abstract or semi-realistic versions of the dental plan displayed on the display 220.

In various embodiments, the computer 210 may include one or more processors, one or more memories, and one or more communication mechanisms. In some embodiments, more than one computer may be used to execute the modules, methods, blocks, and processes discussed herein. Additionally, the modules and processes herein may each run on one or multiple processors, on one or more computers; or the modules herein may run on dedicated hardware. The input devices 230 may include one or more keyboards (one-handed or two-handed), mice, touch screens, voice commands and associated hardware, gesture recognition, or any other means of providing communication between the operator 240 and the computer 210. The display 220 may be a two-dimensional ("2D") or 3D display and may be based on any technology, such as LCD, CRT, plasma, projection, etc.

The communication among the various components of system 200 may be accomplished via any appropriate coupling, including USB, VGA cables, coaxial cables, FireWire, serial cables, parallel cables, SCSI cables, IDE cables, SATA cables, wireless based on 802.11 or Bluetooth, or any other wired or wireless connection(s). One or more of the components in system 200 may also be combined into a single unit or module. In some embodiments, all of the electronic components of system 200 are included in a single physical unit or module.

Example Process for Library Selection in Dental Prosthesis Design

Various embodiments of process 300 enable an operator to select tooth morphologies or libraries of tooth morphologies to be used in a dental design. Process 300 may take place as a required step in a dental design process or it may be an option step in a dental design process, such as the one described in U.S. patent application Ser. No. 12/703,601, filed Feb. 10, 2010, entitled Dental Prosthetics Manipulation, Selection, and Planning, which is incorporated by reference above in its entirety for all purposes.

Process 300 begins by presenting two or more dental libraries as well as a dental plan in block 310. Presenting the two or more dental libraries may take many forms. For example, as shown in FIG. 1, the two or more dental libraries can be shown vertically stacked in a library selection portion 110. Other methods and techniques of showing the libraries may include cascading the libraries, tiling the libraries, and the like. In some embodiments, the tooth morphologies are represented in the library selection portion by presenting abstract representations of the individual tooth morphologies. These abstract representations may be icons, pictures, etc. In some embodiments, these icons or pictures are similarly shaped to the morphology itself. Relatedly, in some embodiments, when the operator selects a morphology to place into the dental plan, the operator may actually be selecting the icon or picture of the tooth morphology.

Figure 3:
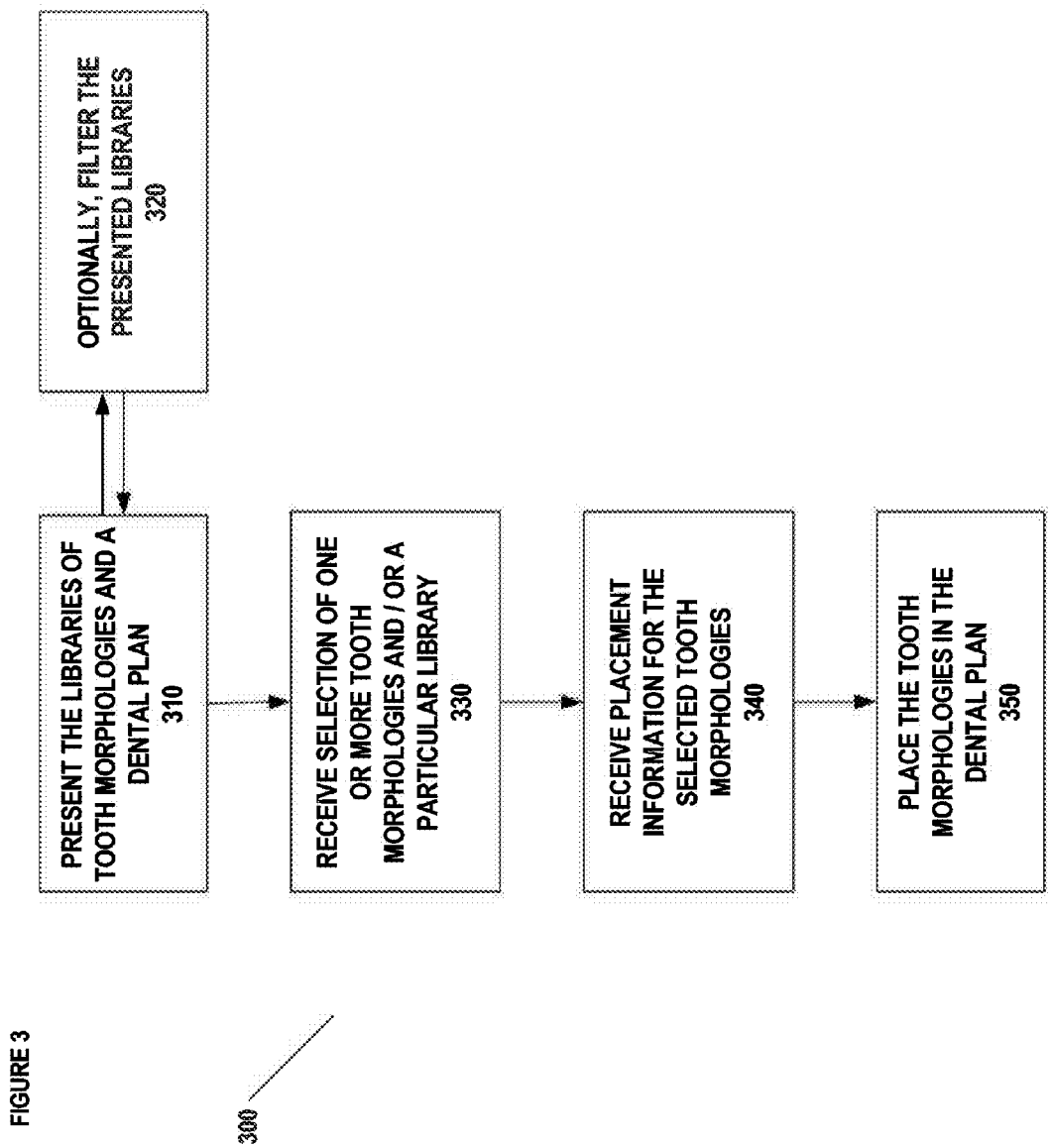
FIG. 3 illustrates a method for library selection in dental prosthesis design.

Block 310 can also include presenting the dental plan to the operator. As illustrated in FIG. 1, a dental plan can be shown, in the desired dental plan portion 140, as an expanded abstract representation of the upper and lower sets of teeth. Other representations may also be used. For example, in some embodiments, a dental plan may be shown as a semi-realistic representation of the teeth in their relative positions, similar to representation of the upper and lower human jaw. In some embodiments, only the maxillary set of teeth or a subset of the maxillary set of teeth of a dental plan is shown in the desired dental plan portion 140. In some embodiments, only the mandibular set of teeth or a portion of the mandibular set of teeth is shown in the desired dental plan portion 140. In yet other embodiments, an operator may select what portions of the dental plan are shown in block 310 (not shown in FIG. 3).

In some embodiments, filters are provided that allow the operator to filter which tooth morphologies are shown in the library selection portion 110. Filtering can happen as part of block 320. For example, as shown in FIG. 1, one or more filters may be presented in the library filter portion 120. These filters can be any appropriate filter including those that would limit the number of libraries of tooth morphologies. For example, a company filter may limit the libraries shown to only those from a particular company or companies. An arch filter may limit the number of libraries shown to only those libraries or only portions of libraries that correspond to the upper arch or the lower arch (sometimes known as the maxillary arch and mandibular arch, respectively).

A position filter may also be provided in some embodiments. The position filter may limit the tooth morphologies shown in the libraries to only those in the anterior and/or posterior portions of the mouth. Additionally, a position filter may allow the operator to limit the morphologies shown to only those at particular positions. A library filter may also be provided in which the operator may be able to limit the libraries shown to only those that match a certain characteristic of libraries or with certain library names. The library filter may be useful if the operator knows the characteristics of the libraries or the library names but is unfamiliar with the company that might be associated with those characteristics or names.

Figure 7:
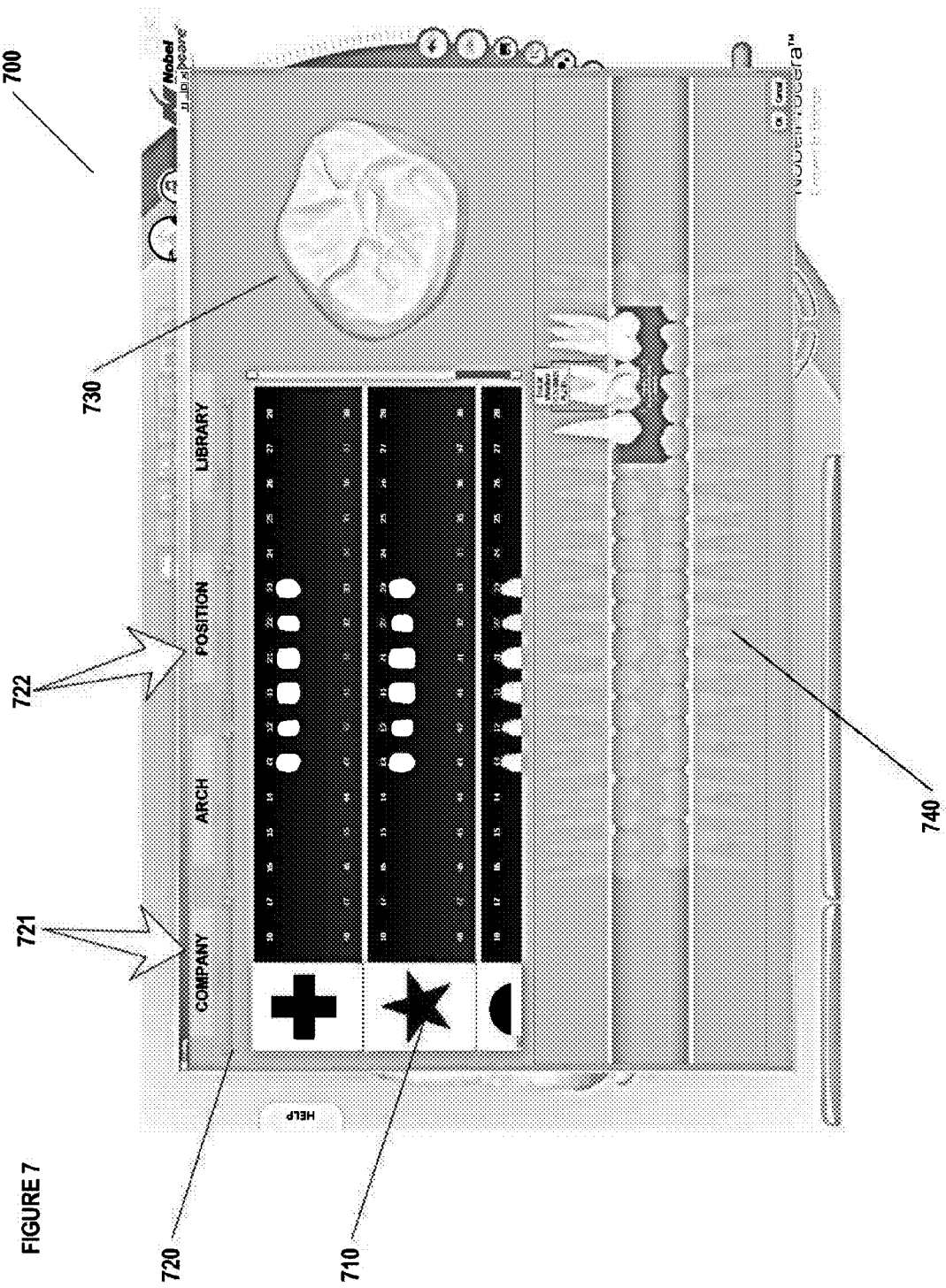
FIG. 7 illustrates a fifth interface for library selection in dental prosthesis design.

In some embodiments, the operator may filter based on two or more of the filters, and only those libraries or tooth morphologies corresponding to both filters may be shown. For example, consider FIG. 7, which illustrates an interface 700 that includes a library filter portion 720, a library selection portion 710, a desired dental plan portion 740, and a preview portion 730. If an operator filters the libraries by company 721 and position 722, then the library selection portion 710 will display in the library selection portion 710 only tooth morphologies corresponding to the selected position that are made by the selected company (corresponding to the position filter 722 and the company filter 721).

Filtering can take many forms in various embodiments, including using a drop-down list, allowing the operator to search and select using text, using radio boxes, or any other appropriate technique.

Figure 5:
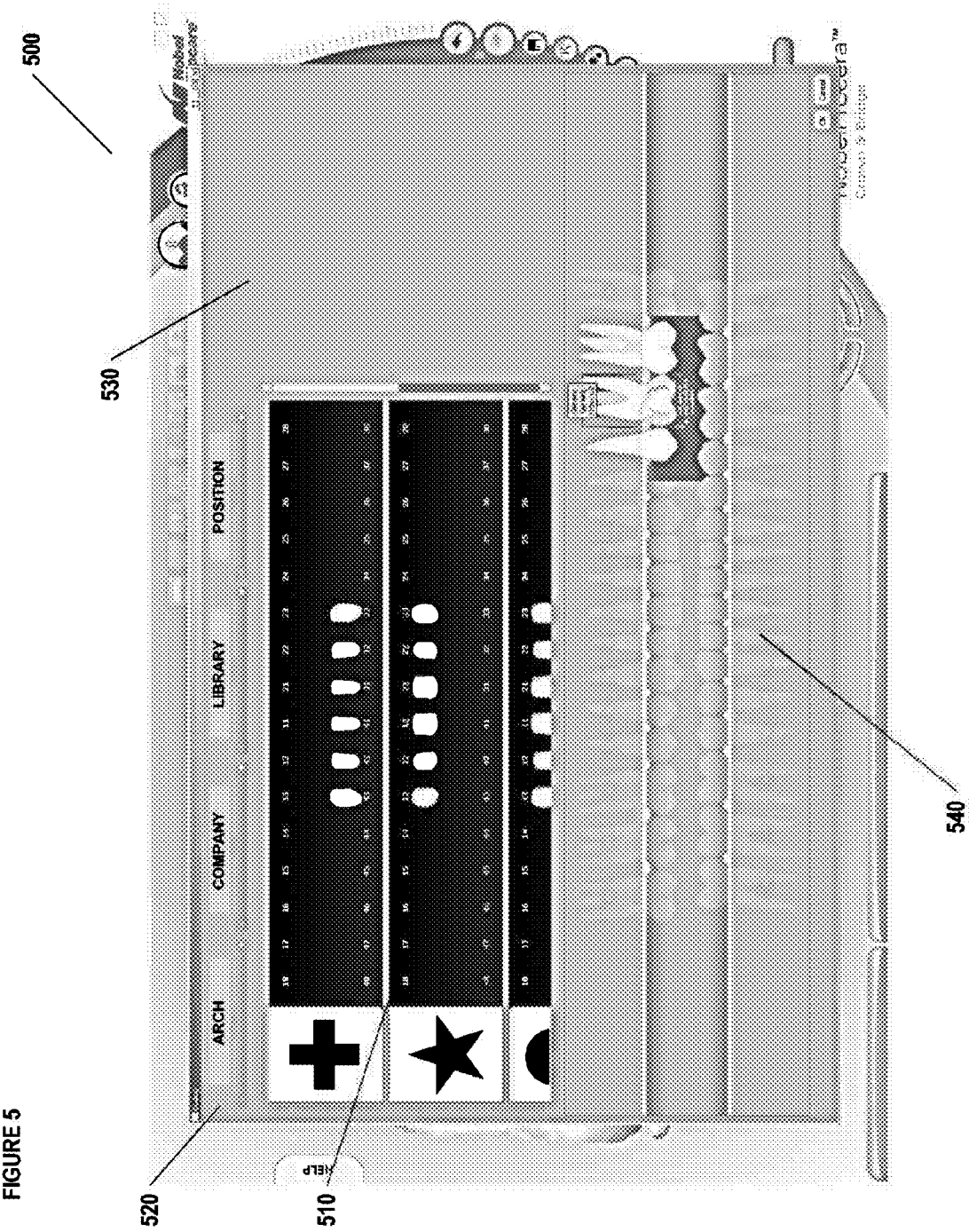
FIG. 5 illustrates a third interface for library selection in dental prosthesis design.

After the libraries have been filtered in block 320, the filtered libraries may be presented in block 310, as described above. In block 330, a selection from the operator of a particular library and/or one or more tooth morphologies in a library may be received. For example, in some embodiments, receiving the selection may correspond to an operator selecting with a mouse or keyboard one or more tooth morphologies in the library or selecting the entire library. Receiving the selection of one or more tooth morphologies and/or an entire library may include the operator selecting with a mouse, keyboard, or other instrument one or more tooth morphologies from a particular library. As illustrated in FIG. 5, in some embodiments, preview portion 530 may remain empty until a tooth morphology has been selected in the library selection portion 510. For example, in FIG. 1, a tooth morphology preview is shown in the preview portion 130 for the tooth selected in the library selection portion 110.

After there has been a selection of a library and/or one or more tooth morphologies in block 330, the operator will provide, and the system will receive, placement information for the selected tooth morphologies or library in block 340. Receiving placement information can take many forms. For example, in some embodiments, the operator may "drag" using the mouse, a particular tooth morphology to a particular position in the desired dental plan, shown in the desired dental plan portion, such as desired dental plan portion 140 of FIG. 1. The operator may also be able to drag two or more tooth morphologies to the desired dental plan to replace the tooth morphologies in two or more positions. In some embodiments, in order to select a particular library of tooth morphologies for use in all active positions of the desired dental plan, the operator may drag one or more selected tooth morphologies or an entire selected library into the desired dental plan portion 140, but not over any active tooth position in the desired dental plan.

In some embodiments, other options for providing placement information include the operator providing keystrokes indicating particular positions in the dental plan or a combination of keystrokes and mouse movements, such as moving the mouse over a particular unit in the dental plan and striking control V or other keystroke in order to indicate placement at that particular unit or position.

Figure 6:
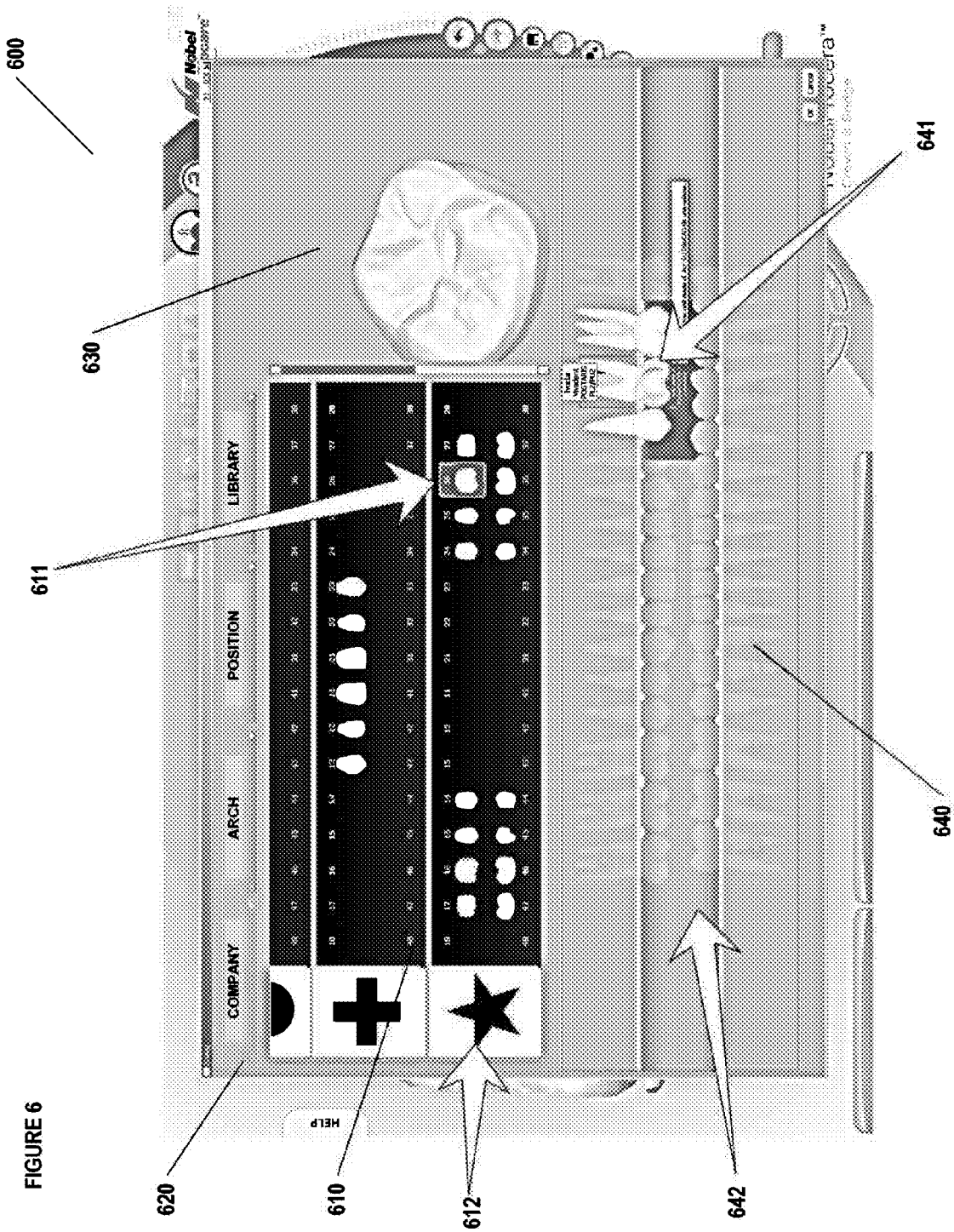
FIG. 6 illustrates a fourth interface for library selection in dental prosthesis design.

As an example of selection and placement of tooth morphologies, consider FIG. 6 which illustrates an interface 600 that has a library filter portion 620, a library selection portion 610, a dental plan portion 640, and a preview portion 630. Once a particular tooth morphology 611 is selected in library selection portion 610, a preview of that tooth may be shown in 3D, or in other manner, either realistically or semi-realistically in preview portion 630. In some embodiments, the operator may then drag and drop the selected tooth morphology 611 to a particular position 641 in the desired dental plan portion 640. In some embodiments, an operator may select a particular tooth morphology 611 and place the particular tooth morphology into the desired dental plan at a particular position 641 using mouse movements or with the keyboard (e.g., by typing in a tooth position), performing combinations of mouse and keystrokes or by any other method.

In some embodiments, the operator may be able to replace the tooth morphologies for an entire dental plan by selecting anywhere in the library selection portion 610, such as at tooth morphology 611 or tooth morphology library identifier 612, and dragging the entire dental plan to any position outside the teeth positions that are active in the desired dental plan, such as a position that is not above any teeth, position 642 in the desired dental plan portion 640. This may replace all of the tooth morphologies in the desired dental plan. As above, other techniques for selecting and placing the desired tooth morphology library into the desired dental plan may be used, such as combinations of mouse movements, combinations of keystrokes and/or combinations of mouse movements combined with keystrokes. In some embodiments, an operator may select a tooth morphology with a first unit number, such as tooth morphology 611, and may place that tooth morphology in the desired dental plan at a second unit number that is different from the first unit number. For example, not shown in FIG. 6, if the operator selected tooth number 27 from the tooth morphology library and placed it in tooth position 26, then the tooth morphology used in the dental plan at tooth position 26 would be that of the selected tooth morphology position 27, notwithstanding that the two are different.

Returning again to FIG. 3, after placement information has been received for the selected tooth morphology in block 340, the tooth morphologies will be placed in the dental plan in block 350. Placing the tooth morphologies in the dental plan may comprise altering a computer model, data structure, or other computer-based representation of the dental plan. For example, in some embodiments, a system such as system 200 will store in memory an abstract data representation of the desired dental plan. After the operator selects a tooth morphology or an entire library in block 330 and provides placement information for the selected library or tooth morphologies in block 340, then in block 350 a computer system 200 may modify the abstract representation or model of the dental plan in the underlying memory. In some embodiments, not shown in FIG. 3, the representation of the dental plan shown in the desired dental plan portion may be modified after the tooth morphology or library has been placed in block 350.

The blocks of process 300 may be performed in a different order, may be augmented by other blocks or may have sub-blocks within the blocks shown. Further, the process 300 may be performed on a single computer or processor, on multiple computers or processors, on a single or multiple virtual machines, and/or in a distributed fashion on multiple processors, machines, or virtual machines.

The process 300 may be performed as part of a dental prosthesis design system, such as embodiments described in U.S. patent application Ser. No. 12/703,601, filed Feb. 10, 2010, entitled Dental Prosthetics Manipulation, Selection, and Planning, which was incorporated above. The morphology selection may happen as an integral part of the dental prosthesis design or an optional step in dental prosthesis design. For example, a user or operator may be able to design a dental prosthesis such as a full anatomic restoration in order to see an interim result for the design. If the user or operator would like to change the outcome, the operator may want to change the morphology or the morphologies used in the dental prosthesis design. The operator may press a button, select an icon on an interface or otherwise initiate the library selection process in order to choose one or more new morphologies to use in the dental design.

Figure 4:
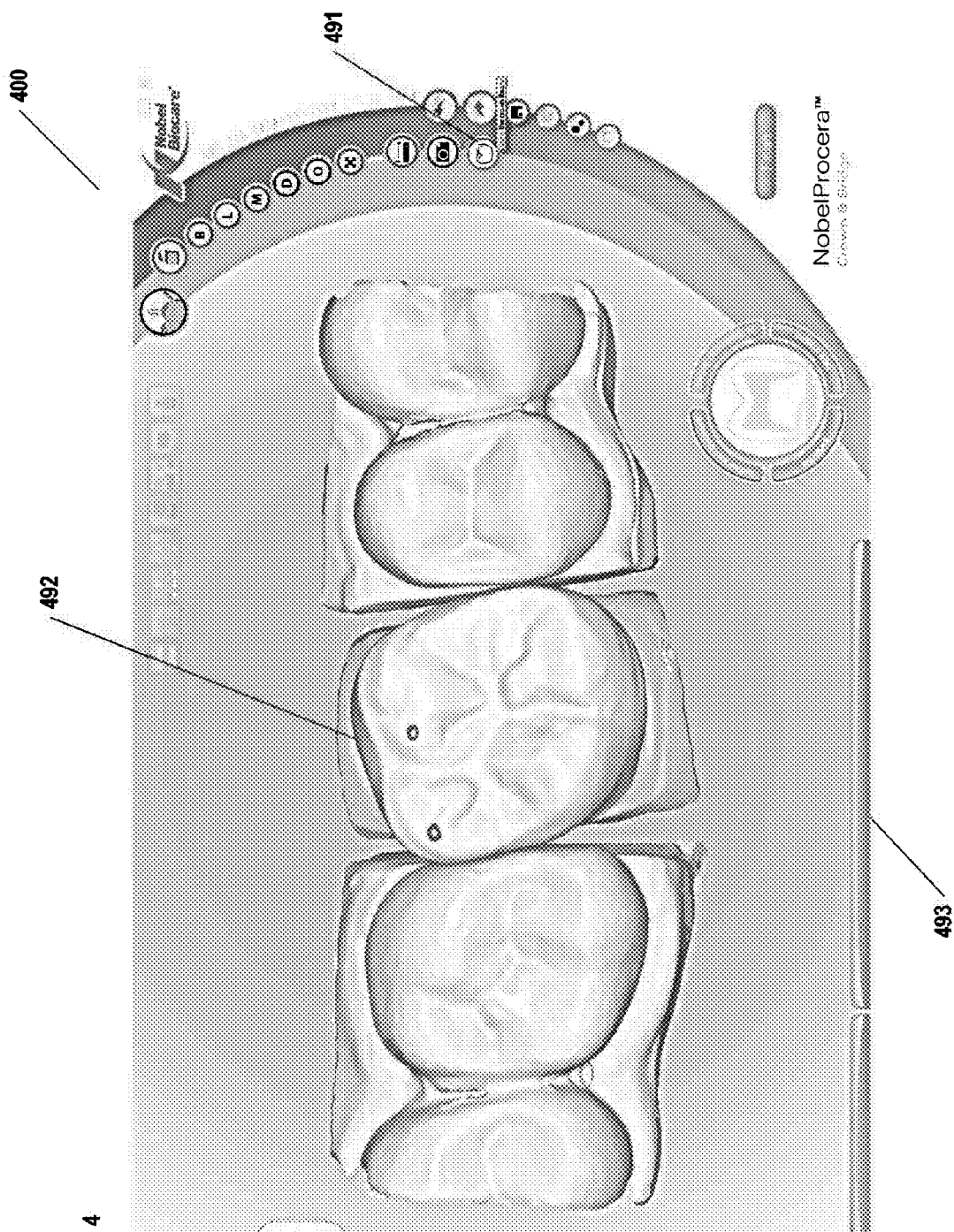
FIG. 4 illustrates a second interface for library selection in dental prosthesis design.

For example, referring now to FIG. 4, if an operator is designing a dental prosthesis 492 on an interface 400 then the user or operator may wish to change the morphology of the dental prosthesis 492. The operator may be able to select or click on a button 491 in order to open the library selection interface. In some embodiments, the library selection interface may be accessible using other means such as keystroke or a pull-in menu or window, such as example of pull-in window 493 (shown as the tab to pull in the window in FIG. 4).

Additional Embodiments

Figure 8:
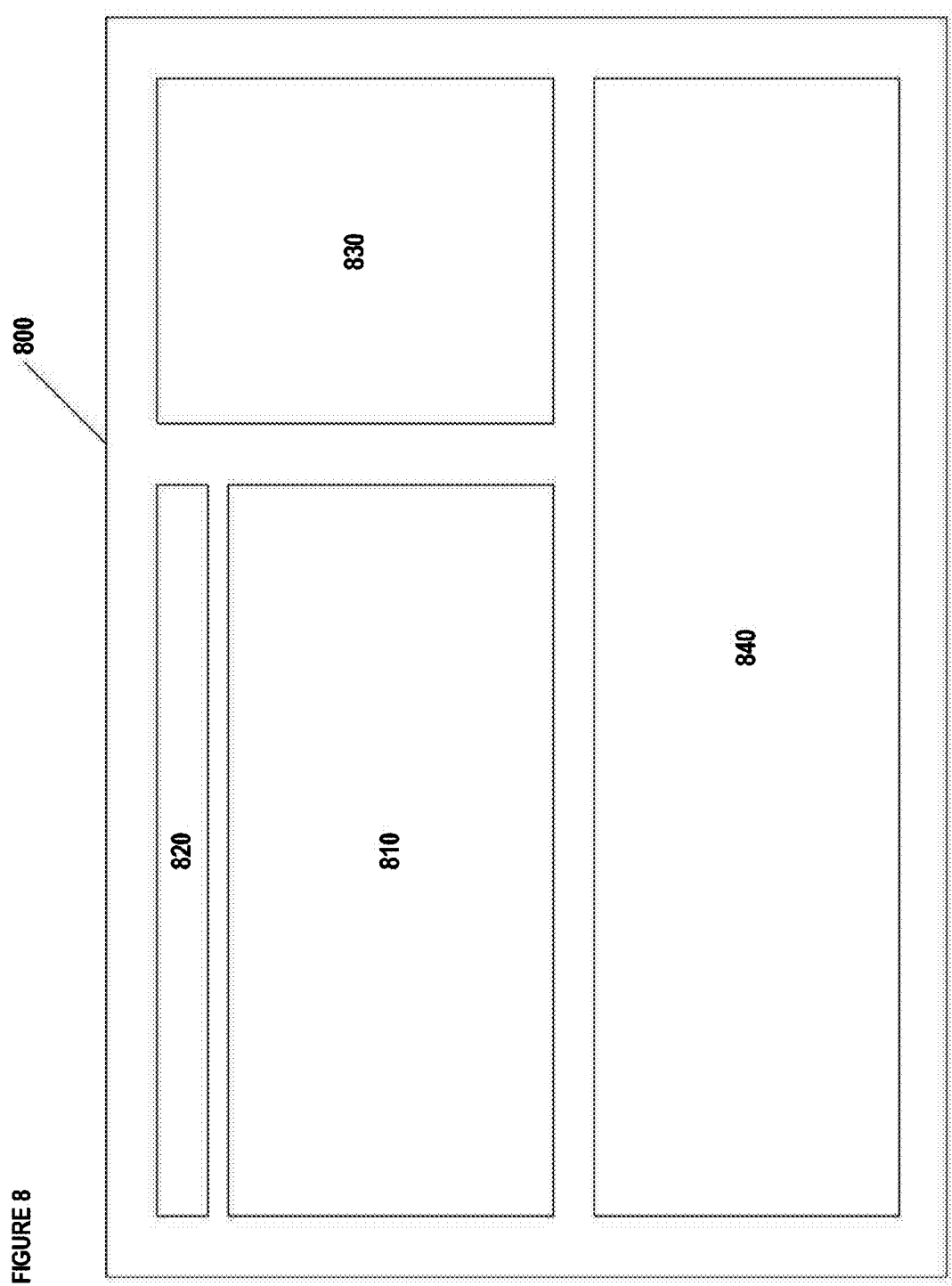
FIG. 8 illustrates a sixth interface for library selection in dental prosthesis design.

All of the portions of an interface for library selection in dental prosthesis design may be displayed on a single display or they may be displayed on multiple displays. For example, turning to FIG. 8, which is an abstract representation of an interface 800 for library selection in dental prosthesis design, interface 800 includes a library filter portion 820, a library selection portion 810, a preview portion 830, and a desired dental plan portion 840. All of these are presented on the same interface, for example, on the same display or in the same window. The portions of the interfaces described herein, in some embodiments, may be presented on more than one interface, some of the portions may not be shown, and/or other portions may be provided. For example, FIG. 9 illustrates a first interface 900 which includes the library filter portion 920, the library selection portion 910, and the desired dental plan portion 940. The second interface 901 may include the preview portion 930. Other combinations of portions and distributions among two or more interfaces are also within the scope herein.

The processes and systems described herein may be performed on or encompass various types of hardware, such as computer systems. In some embodiments, computer 210, display 220, and/or input device 230 may each be separate computer systems, applications, or processes or may run as part of the same computer systems, applications, or processes—or one or more may be combined to run as part of one application or process—and/or each or one or more may be part of or run on a computer system. A computer system may include a bus or other communication mechanism for communicating information, and a processor coupled with the bus for processing information. The computer systems may have a main memory, such as a random access memory or other dynamic storage device, coupled to the bus. The main memory may be used to store instructions and temporary variables. The computer systems may also include a read-only memory or other static storage device coupled to the bus for storing static information and instructions. The computer systems may also be coupled to a display, such as a CRT or LCD monitor. Input devices may also be coupled to the computer system. These input devices may include a mouse, a trackball, or cursor direction keys.

Each computer system may be implemented using one or more physical computers or computer systems or portions thereof. The instructions executed by the computer system may also be read in from a computer-readable medium. The computer-readable medium may be a CD, DVD, optical or magnetic disk, laserdisc, carrier wave, or any other medium that is readable by the computer system. In some embodiments, hardwired circuitry may be used in place of or in combination with software instructions executed by the processor. Communication among modules, systems, devices, and elements may be over a direct or switched connections, and wired or wireless networks or connections, via directly connected wires, or any other appropriate communication mechanism. The communication among modules, systems, devices, and elements may include handshaking, notifications, coordination, encapsulation, encryption, headers, such as routing or error detecting headers, or any other appropriate communication protocol or attribute. Communication may also messages related to HTTP, HTTPS, FTP, TCP, IP, ebMS OASIS/ebXML, secure sockets, VPN, encrypted or unencrypted pipes, MIME, SMTP, MIME Multipart/Related Content-type, SQL, etc.

Any appropriate 3D graphics processing may be used for displaying or rendering including processing based on OpenGL, Direct3D, Java 3D, etc. Whole, partial, or modified 3D graphics packages may also be used, such packages including 3DS Max, SolidWorks, Maya, Form Z, Cybermotion 3D, or any others. In some embodiments, various parts of the needed rendering may occur on traditional or specialized graphics hardware. The rendering may also occur on the general CPU, on programmable hardware, on a separate processor, be distributed over multiple processors, over multiple dedicated graphics cards, or using any other appropriate combination of hardware or technique.

As will be apparent, the features and attributes of the specific embodiments disclosed above may be combined in different ways to form additional embodiments, all of which fall within the scope of the present disclosure.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements, and/or states. Thus, such conditional language is not generally intended to imply that features, elements and/or states are in any way required for one or more embodiments or that one or more embodiments necessarily include logic for deciding, with or without author input or prompting, whether these features, elements, and/or states are included or are to be performed in any particular embodiment.

Any process descriptions, elements, or blocks in the flow diagrams described herein and/or depicted in the attached figures should be understood as potentially representing modules, segments, or portions of code which include one or more executable instructions for implementing specific logical functions or steps in the process. Alternate implementations are included within the scope of the embodiments described herein in which elements or functions may be deleted, executed out of order from that shown or discussed, including substantially concurrently or in reverse order, depending on the functionality involved, as would be understood by those skilled in the art.

All of the methods and processes described above may be embodied in, and fully automated via, software code modules executed by one or more general purpose computers or processors, such as those computer systems described above. The code modules may be stored in any type of computer-readable medium or other computer storage device. Some or all of the methods may alternatively be embodied in specialized computer hardware.

It should be emphasized that many variations and modifications may be made to the above-described embodiments, the elements of which are to be understood as being among other acceptable examples. All such modifications and variations are intended to be included herein within the scope of this disclosure and protected by the following claims.

What is claimed is:

1. A computer-implemented method for library selection in dental prosthesis design, comprising:
   presenting, via a computer-based interface, two or more dental morphology libraries for use in a dental plan, said computer-based interface running on one or more computer processors;
   receiving filtering information for the dental morphology libraries, wherein receiving filter information for the dental morphology libraries comprises receiving filter information selected from the group consisting of company, arch, position, and library;
   receiving via the computer-based interface a selection of one or more tooth morphologies from among the tooth morphologies in a particular dental morphology library, said particular dental morphology library being selected from among the two or more dental morphology libraries;
   receiving via the computer-based interface placement information in the dental plan for the one or more tooth morphologies; and
   placing the one or more tooth morphologies in the dental plan.

2. The method of claim 1, wherein the method further comprises generating production data based at least in part on the placed one or more tooth morphologies.

3. The method of claim 1, wherein the method further comprises:
   selecting which libraries among the two or more dental morphology libraries to provide via the computer-based interface for selection at least in part based on the filtering information.

4. The method of claim 1, wherein the method further comprises providing via the computer-based interface a preview of one or more of the one or more selected tooth morphologies.

5. The method of claim 1, wherein receiving placement information for the one or more tooth morphologies comprises receiving information that an operator has selected the particular dental morphology library for all prosthetic teeth in the dental plan.

6. The method of claim 1, wherein receiving the selection of one or more tooth morphologies comprises receiving a selection of a particular tooth morphology and receiving the placement information comprises receiving a particular placement in the dental plan in which to place the particular tooth morphology.

7. The method of claim 1, wherein receiving placement information for the one or more tooth morphologies comprises receiving mouse information from a mouse manipulated by an operator.

8. The method of claim 1, wherein receiving placement information comprises receiving information to place a tooth morphology associated with a first tooth number into the dental plan at a position associated with a second tooth number, wherein the first tooth number and the second tooth number are different.

9. The method of claim 1, wherein the method further comprises:
   receiving a second selection of one or more tooth morphologies from among the tooth morphologies in a second dental morphology library, wherein said second dental morphology library is selected from among the two or more dental morphology libraries, and wherein said second dental morphology library is different from the particular morphology library;
   receiving second placement information in the dental plan for the second selection of one or more tooth morphologies; and
   placing the second selection of one or more tooth morphologies in the dental plan.

10. The method of claim 1, wherein the dental plan is for a full anatomic restoration.

11. The method of claim 1, wherein the dental plan is for a cutback restoration.

12. A system for library selection in dental prosthesis design, comprising:
one or more computer processors configured to:
present, via a computer-based interface, two or more dental morphology libraries for use in a dental plan, said dental plan being stored in one or more memories coupled to the one or more computer processors;
receive, via the computer-based interface, a selection of one or more tooth morphologies from among the tooth morphologies in a particular dental morphology library, said particular dental morphology library being selected from among the two or more dental morphology libraries;
receive filtering formation for the dental morphology libraries wherein receiving filter information for the dental morphology libraries comprises receiving filter information selected from the group consisting of company, arch, position, and library;
receive, via the computer-based interface, placement information in the dental plan for the one or more tooth morphologies; and
place the one or more tooth morphologies in the dental plan by, at least in part, modifying data in the one or more memories.

13. The system of claim 12, wherein the one or more processors are further configured to generate production data based on the placed one or more tooth morphologies.

14. The system of claim 12, wherein the one or more processors are further configured to:
select which libraries among the two or more dental morphology libraries to provide via the computer-based interface for selection at least in part based on the filtering information.

15. The system of claim 12, wherein the received placement information for the one or more tooth morphologies comprises a selection of the particular dental morphology library for all prosthetic teeth in the dental plan.

16. The system of claim 12, wherein the received placement information for the one or more tooth morphologies comprises a selection of a particular tooth morphology and a particular placement in the dental plan in which to place the particular tooth morphology.

17. A non-transistory computer-readable storage media for library selection in dental prosthesis design, said non-transistory computer-readable storage medium containing instructions, said instructions operable to execute on a computer system, said instructions when executing on the computer system performing a method comprising:
presenting, via a computer-based interface, two or more dental morphology libraries for use in a dental plan;
receiving via the computer-based interface a selection of one or more tooth morphologies from among the tooth morphologies in a particular dental morphology library, said particular dental morphology library being selected from among the two or more dental morphology libraries;
receiving filtering information for the dental morphology libraries, wherein receiving filter information for the dental morphology libraries comprises receiving filter information selected from the group consisting of company, arch, position, and library;
receiving via the computer-based interface placement information in the dental plan for the one or more tooth morphologies; and
placing the one or more tooth morphologies in the dental plan.

18. The non-transistory computer-readable storage media of claim 17, wherein the method performed on the computer system when executing the instruction stored on the non-transistory computer-readable storage media further comprises generating production data based on the placed one or more tooth morphologies.

19. The non-transistory computer-readable storage media of claim 17, wherein the method performed on the computer system when executing the instruction stored on the non-transistory computer-readable storage media further comprises:
selecting which libraries among the two or more dental morphology libraries to provide via the computer-based interface for selection at least in part based on the filtering information.

* * * * *

UNITED STATES PATENT AND TRADEMARK OFFICE
CERTIFICATE OF CORRECTION

PATENT NO. : 8,949,730 B2  
APPLICATION NO. : 12/835936  
DATED : February 3, 2015  
INVENTOR(S) : David Giasson Page 1 of 1

It is certified that error appears in the above-identified patent and that said Letters Patent is hereby corrected as shown below:

Claims

In column 11 at line 14, In Claim 12, change "formation" to --information--.

In column 11 at line 15, In Claim 12, change "libraries wherein" to --libraries, wherein--.

In column 12 at line 1, In Claim 17, change "non-transistory" to --non-transitory--.

In column 12 at lines 2-3, In Claim 17, change "non-transistory" to --non-transitory--.

In column 12 at line 25, In Claim 18, change "non-transistory" to --non-transitory--.

In column 12 at lines 27-28, In Claim 18, change "non-transistory" to --non-transitory--.

In column 12 at lines 33-34, In Claim 19, change "non-transistory" to --non-transitory--.

Signed and Sealed this  
Third Day of November, 2015

Michelle K. Lee  
*Director of the United States Patent and Trademark Office*